US006515109B1

(12) United States Patent
Ollmann et al.

(10) Patent No.: US 6,515,109 B1
(45) Date of Patent: Feb. 4, 2003

(54) HUMAN ECT2 POLYPEPTIDE

(75) Inventors: Michael Martin Ollmann, Redwood City, CA (US); Kevin Patrick Keegan, San Diego, CA (US); Thomas J. Stout, San Francisco, CA (US); David Matthews, San Francisco, CA (US); Alison Joly, San Mateo, CA (US)

(73) Assignee: Exelixis, Inc., S. San Francisco, CA (US)

( * ) Notice: Subject to any disclaimer, the term of this patent is extended or adjusted under 35 U.S.C. 154(b) by 0 days.

(21) Appl. No.: 09/976,239

(22) Filed: Oct. 12, 2001

Related U.S. Application Data

(60) Provisional application No. 60/239,689, filed on Oct. 12, 2000.

(51) Int. Cl.[7] ............................................. C07K 14/00
(52) U.S. Cl. ...................................................... 530/350
(58) Field of Search ................................. 530/350, 300

(56) References Cited

PUBLICATIONS

Lehner, C.F., "The pebble gene is required for cytokinesis in Drosophila", Journal of Cell Science, 1992, 103:1021–1030, The Company of Biologists Limited, Great Britain.
Hedge,P., et al., "EST377993 MAGE resequences, MAGI Homo sapiens cDNA, mRNA sequence" Genbank GI No. 8155756, Jun. 1, 2000.
NCI–CGAP, "tu89e03.x1 NCIaCGAPaGas4 Homo sapiens cDNA clone IMAGE:2258236 3' similar to TR:Q07139 Q07139 ECT2 Oncogene" Genbank GI No. 5636530, Dec. 15, 1999.
NIH–MGC, "UI–HF–BN0–aln–c–10–0OU1.r1 NIHaMGCa50 Homo sapiens cDNA clone IMAGE:3080082 5" Genbank GI No. 7142453, Mar. 2, 2000.
Dias Neto, E., "QV1–BT0631–150200–071–f05 BT0631 Homo sapiens cDNA, mRNA squence" Genbank GI No. 8471000, Jun. 12, 2000.
NIH–MGC, "UI–HF–BN0–ala–h–11–0–U1.r1 NIHaMGCa50 Homo sapiens cDNA clone IMAGE:3079149 5" Genbank GI No. 7142100, Mar. 2, 2000.
Dias Neto, E., "QV1–BT0631–280200–084–d11 BT0631 Homo sapiens cDNA" Genbank GI No. 8471150, Jun. 12, 2000.
Hegde P., "EST382885 MAGE resequences, MAGK Homo sapiens cDNA" Genbank GI No. 8160647, Jun. 1, 2000.
NCI–CGAP, "zs92g10.r1 NCIaCGAPaGCB1 Homo sapiens cDNA clone IMAGE:7040994 5' similar to TR:G293332 G293332 ECT2 Protein. mRNA sequence" Genbank GI No. 1921407, Aug. 15, 1997.
Hillier,L., "zq51a07.r1 Stratagene neuroepithelium (#937231) Homo sapiens cDNA clone IMAGE:645108 5' similar to TR:G293332 G293332 ECT2 Protein" Genbank GI No. 1801929, Jan. 27, 1997.
Adams,M.D., "est185199 Colon Carcinoma (HCC) cell line Homo sapiens cDNA 5' end similar to similar to transforming protein, mRNA sequence" Genbank GI No. 1965630, Apr. 19, 1997.
Miki, T., "Mouse oncogene (ect2) mRNA, complete cds-"GenbankGI No. 293331, Jun. 12, 1999.
Miki, T., "ect2" Genbank GI No. 293332, Jun. 12, 1993.
Miki, T., "Mouse oncogene (ect2) mRNA, complete cds" Genbank GI No. 293331, Jun. 12, 1993.
Tatsumoto et al, Human ECT2 is an exchange factor for Rho GTPases, phosphorylated in G2/M phases, and involved in cytokinesis. J. Cell Biol. 147: 921–927, 1999.*

* cited by examiner

*Primary Examiner*—Elizabeth Kemmerer
*Assistant Examiner*—Ruixiang Li
(74) *Attorney, Agent, or Firm*—Jan P. Brunelle; Laleh Shayesteh

(57) ABSTRACT

Human Ect2 polypeptide, fragments and derivatives, along with vectors and host cells for expression and production of Ect2 polypeptide are provided. Various methods of screening for agents that modulate interaction of Ect2 with an Ect2 binding agent, including high throughput methods, are also provided.

1 Claim, No Drawings

HUMAN ECT2 POLYPEPTIDE

REFERENCE TO RELATED APPLICATIONS

This Application claims priority to U.S. provisional patent application serial No. 60/239,689, filed Oct. 12, 2000, the contents of which are hereby incorporated in its entirety.

BACKGROUND OF THE INVENTION

The superfamily of small (21 kDa) GTP binding proteins (small G proteins) comprises subfamilies: Ras, Rho, ADP ribosylation factors (ARFs), Rab, and Ran, which act as molecular switches to regulate numerous cellular responses. Members of the Rho family of GTPases, include RhoA, -B, and -C, Rac1 and -2, and Cdc42. Guanine nucleotide exchange factors (GEFs) activate Rho proteins by catalyzing the replacement of bound GDP with GTP. The GTP-bound form of Rho proteins specifically interact with their effectors or targets and transmit signals to downstream molecules. Rho proteins are inactivated through the hydrolysis of bound GTP to GDP by intrinsic GTPase activity, assisted by GTPase activating proteins (GAPs). The Rho family of GTPases participate in regulation of the actin cytoskeleton and cell adhesion, and are also involved in regulation of smooth muscle contraction, cell morphology, cell motility, neurite retraction, cytokinesis, and cell transformation (Hall, A. Science (1998) 279:509–514).

Ect2, a transforming protein with sequence similarity to the dbl homology (DH) domain proteins, is a GEF that associates with a subset of the Rho family proteins: RhoA, Cdc42, and Rac1. Ect2 phosphorylation, which is required for its exchange activity, occurs during G2 and M phases. Human Ect2 is involved in the regulation of cytokinesis. The human ect2 gene is located on the long arm of chromosome 3, at 3q26 (Takai S, et al., Genomics (1995) 27(1):220–222), a region of increased copy number and expression in a large number of cancers (Bitter M A, et al., Blood (1985) 66(6):1362–1370; Kim D H, et al., Int J Cancer. (1995) 60(6):812–819; Brzoska P M, et al., Cancer Res. (1995) 55(14):3055–3059; Balsara B R, et al., Cancer Res. (1997) 57(11):2116–2120; Heselmeyer K, et al., Genes Chromosomes Cancer (1997) 19(4):233–240; Sonoda G, et al., Genes Chromosomes Cancer. (1997) 20(4):320–8). Data available from the National Cancer Institute indicates that human ect2 is overexpressed in cancers of the ovary, uterus, parathyroid, testis, brain, and colon.

The ect2 gene is conserved at the sequence and functional levels in mammals and insects. The pebble gene in Drosophila (GenBank ID # (GI) 5817603) is the orthologue of mouse (GI293331) and human ect2, and is required for initiation of cytokinesis (Lehner C F, J. Cell Sci. (1992) 103: 1021–1030; Prokopenko S N, et al., Genes Dev (1999) 13(17):2301–2314).

SUMMARY OF THE INVENTION

The invention provides isolated human Ect2 protein and its splice variant as well as fragments and derivatives thereof. Vectors and host cells expressing Ect2 molecules, as well as methods of production of Ect2 and methods of production of cells for expressing Ect2 are also described.

The invention further provides methods of screening for agents that modulate the interaction of an Ect2 polypeptide with an Ect2 binding target. In one aspect, the screening method comprises the steps of expressing a recombinant Ect2 polypeptide, incubating the polypeptide and the Ect2 binding target with a candidate agent and determining whether the candidate agent modulates the binding of the Ect2 polypeptide with the Ect2 binding target. Preferred modulating agents include Ect2-specific antibodies and small molecules identified in high throughput screens.

The invention further provides novel high throughput assays to measure Ect2 activity.

DETAILED DESCRIPTION OF THE INVENTION

The ability to screen or manipulate the genomes of model organisms provides a powerful means to analyze complex genetic pathways. In particular, overexpression screens in Drosophila enable quick identification of genes involved in the same or overlapping pathways as human genetic pathways (Rorth P., et al., Development (1998) 125:1049–1057; WO0015843). We performed an overexpression screen in Drosophila to identify genes that interact with the cyclin dependent kinase inhibitor, p21 (Bourne H R, et al., Nature (1990) 348(6297):125–132; Marshall C J, Trends Genet (1991) 7(3):91–95). Pebble, the Drosophila orthologue of human Ect2, was identified as a suppressor of p21 overexpression. To our knowledge, there are no prior reports in the literature of a link between Ect2 and the G1 phase of the cell cycle, or any evidence that suggests that overexpression of Ect2 can overcome a block in the cell cycle. Our identification of an Ect2 orthologue in the Drosophila p21 screen supports both conclusions. Thus, Ect2 is a valuable "target" that can be used to identify compounds and other agents that modulate its function, and thus have utility in treatment of disease or disorders associated with defective cell cycle progression at G1 phase, and in particular, defective p21 function.

Ect2 Nucleic Acids and Polypeptides

We identified cDNA sequences of human ect2 and a splice variant (SEQ ID NO:1 and SEQ ID NO:3, respectively) through bioinformatic analysis of public databases and "contigging" several incomplete EST sequences (AW965920, AI916675, AW504786, BE080710, AW504433, BE080860, AW970802, AA279942, AA206473, AA313301). Northern Blot analysis of mRNA from tumor samples, using full or partial ect2 cDNA (SEQ ID Nos:1 and 3) sequences as probes (Current Protocol in Molecular Biology, Eds. Asubel, et al., Wiley Interscience, NY), can identify tumors that overexpress Ect2, and that, therefore, are amenable to treatment by inhibition of Ect2 function. Alternatively, quantitative PCR, such as the TaqMan® procedure (PE Applied Biosystems) is used for analysis of Ect2 expression in tumor samples.

The term "Ect2 polypeptide" refers to a full-length Ect2 protein or a fragment or derivative thereof. A preferred Ect2 polypeptide comprises or consists of an amino acid sequence of SEQ ID NO:2 or 4, or a fragment or derivative thereof. Compositions comprising Ect2 polypeptides may consist essentially of the Ect2 protein, fragment, or derivative, or may comprise additional components (e.g. pharmaceutically acceptable carriers or excipients, culture media, etc.).

Ect2 protein derivatives typically share a certain degree of sequence identity or sequence similarity with SEQ ID NOs:2 or 4, or a fragment thereof. As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Preferred Ect2 protein derivatives or fragments share at least 80% sequence identity or similarity, preferably at least 85%, more preferably at least 90%, still more preferably at least 95%, and most preferably 97% or 100% sequence identity or similarity with a contiguous stretch of at least 25, 50, 100, 224, or 234 amino acids of SEQ ID NO:2 or 4, and in some cases, the entire length of SEQ ID NO:2 or 4. Preferred derivatives or fragments of Ect2 consist of or comprise an amino acid sequence that has at least 80%, preferably at least 85%, more preferably at least 90%, still more preferably at least 95%, and most preferably 100% sequence identity or sequence similarity with any of amino acid residues 147–227 (BRCT domain), 235–323 (BRCT domain), 327–330 (CDC2 consensus site), 419–617 (RHOGEF domain), 636–765 (PH domain), and 814–817 (CDC2 consensus site) of SEQ ID NO:2, or with any amino acid residues 178–258 (BRCT domain), 266–354 (BRCT domain), 358–361 (CDC2 consensus site), 450–648 (RHOGEF domain), 667–796 (PH domain), and 845–848 (CDC2 consensus site) of SEQ ID NO: 4. Each one of the above domains was identified using the pfam program (Bateman et al., Nucleic Acids Res. (1999) 27:260–262) which also contains the detailed description of each domain (BRCT domain: PF00533; RHOGEF domain: PF00621; PH domain: PF00169).

The fragment or derivative of the Ect2 protein is preferably "functionally active" meaning that it exhibits one or more functional activities associated with a full-length, wild-type Ect2 protein comprising the amino acid sequence of SEQ ID NOs:2 or 4. As one example, a fragment or derivative may have antigenicity such that it can be used in immunoassays, for immunization, for modulation of Ect2 activity, etc, as discussed further below regarding generation of antibodies to Ect2 proteins. Preferably, a functionally active Ect2 fragment or derivative is one that displays one or more biological activities associated with Ect2 proteins, such as signaling activity, binding to small GTPases and/or catalysis of GDP/GTP exchange in small GTPases. If Ect2 fragments are used in assays to identify modulating agents, the fragments preferably comprise one or more of the above-mentioned Ect2 domains, or a C- or N-terminus, and preferably comprise at least 10, 20, 25, 50, 224, or 234 contiguous amino acids of SEQ ID NO:1 or 2.

The term "Ect2 nucleic acid" refers to a DNA or RNA molecule that encodes an Ect2 polypeptide. Preferably, the Ect2 polypeptide or nucleic acid or fragment thereof is from a human (e.g. SEQ ID NOs 1–4), but it can be an ortholog or derivative thereof, preferably with at least 70%, 80%, 85%, 90%, or 95% sequence identity with any one of SEQ ID NOs 1–4. Orthologs can be identified by BLAST analysis using SEQ ID NO:2 or 4, using methods known in the art (Huynen M A and Bork P, Proc Natl Acad Sci (1998) 95:5849–5856; Huynen M A et al., Genome Research (2000) 10:1204–1210).

Isolation, Production, and Expression of Ect2 Nucleic Acids and Polypeptides

A wide variety of methods are available for obtaining Ect2 polypeptides. In general, the intended use for the polypeptide will dictate the particulars of expression, production, and purification methods. For instance, production of polypeptides for use in screening for modulating agents may require methods that preserve specific biological activities of these proteins, whereas production of polypeptides for antibody generation may require structural integrity of particular epitopes. Expression of polypeptides to be purified for screening or antibody production may require the addition of specific tags (i.e., generation of fusion proteins). Techniques for the expression, production, and purification of proteins are well known in the art; any suitable means therefor may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York; U.S. Pat. No. 6,165, 992).

The nucleotide sequence encoding an Ect2 polypeptide can be inserted into any appropriate vector for expression of the inserted protein-coding sequence. The necessary transcriptional and translational signals, including promoter/enhancer element, can derive from the native ect2 gene and/or its flanking regions or can be heterologous. The ect2 gene may be expressed in prokaryotic or eukaryotic cells. The method of choice depends on the intended use of the protein. In particular, eukaryotic systems are particularly useful when native folding and posttranslational modifications are required. Preferred prokaryotic cells include Escherichia coli and Bacillus subtilis. Preferred eukaryotic cells include mammalian cells (such as human, mouse, monkey or Chinese hamster ovary cells), yeast cells (such as Pichia and Saccharomyces species) and insect cells (such as Drosophila and various lepidopteran cell lines, e.g. Sf9 cells). Cell extracts or supernatants may be purified in order to isolate the Ect2 polypeptide. Preferred purification techniques include HPLC, size exclusion chromatography, cation and anion exchange chromatography, reverse phase chromatography, affinity chromatography and other protein purification techniques known to those skilled in the art.

The Ect2 polypeptide may be optionally expressed as a fusion or chimeric product, joined via a peptide bond to a heterologous protein sequence. For example, to facilitate detection and/or purification of Ect2 polypeptide, the Ect2 expression vector construct may contain one or more antibody epitope coding sequences introduced at the N-terminus, C-terminus of the Ect2 coding region and/or at any position within the gene sequence. Suitable sequences include the Myc epitope, HA epitope, FLAG epitope or polyhistidine epitope (see, e.g Harlow and Lane (1988) Antibodies, A Laboratory Manual, Cold Spring Harbor Laboratory). As another example, the Ect2 polypeptide may be expressed as a fusion protein joined to a transcriptional reporter such as GFP or luciferase. A chimeric protein can be made by ligating the appropriate nucleic acid sequences encoding the desired amino acid sequences to each other in the proper coding frame using standard methods and expressing the chimeric product. A chimeric protein may also be made by protein synthetic techniques, e.g. by use of a peptide synthesizer (Hunkapiller et al., Nature (1984) 310:105–111). In addition, polypeptides corresponding to part of the ect2 sequence may be synthesized in order to identify and investigate specific regions of the protein, or to raise antibodies against the protein. The expressed ect2 protein may be isolated in phosphorylated or non-phosphorylated form. In the case where the non-phosphorylated protein is expressed, it may be desirable to phosphorylate the protein in vitro following purification. Typically, the ect2 protein is incubated with protein kinase in the presence of adenosine triphosphate (ATP) under conditions of buffer composition, temperature and incubation time appropriate for the protein kinase in question. Following phosphorylation, the protein may be used directly or subjected to further purification to separate the phosphorylated form from the non-phosphorylated form.

Structural Analysis of Ect2

Three-dimensional structures of components of the Ect2-G-protein (RhoA/Rac/CDC42) system as studied by single-crystal X-ray crystallography provide insight into the mechanistic details of protein-protein recognition between Ect2 and its target G-protein, the guanine nucleotide exchange activity, and the ability of small-molecule compounds to modulate this activity in a therapeutically beneficial manner.

Various Ect2 polypeptide constructs can be studied by X-ray crystallography such as full-length wild-type human Ect2; full-length human Ect2 with relevant point mutations, as indicated by mechanistic biochemical assays; the sub-construct of the RhoGEF domain of human Ect2 (residues 419–617 of SEQ ID NO:2, or 450–648 of SEQ ID NO:4); constructs of the RhoGEF domain of human Ect2 containing relevant point mutations (enhancing, diminishing, or abrogating GEF activity); the sub-construct of the RhoGEF and PH domains of human Ect2 (residues 419–765 of SEQ ID NO:2, or 450–796 of SEQ ID NO:4); constructs of the RhoGEF and PH domains of human Ect2 containing relevant point mutations (enhancing, diminishing, or abrogating GEF activity); any of the above constructs in their native forms, or with N-terminal tags, or with N-terminal GST fusion proteins; any of the above constructs in phosphorylated or dephosphorylated form; and any of the aforementioned in complex with small-molecule modulators of GEF activity as selected from a compound library.

The crystal structures of these Ect2 polypeptides and complexes are determined through the use of standard techniques (Bergfors, T., Ed., 1999, "Protein Crystallization: Techniques, Strategies, and Tips" International University Line, La Jolla, Calif., USA). Crystallizations are accomplished through the screening of "crystallization space" using standard techniques of "Incomplete Factorial Screening" in a variety of crystallization geometries such as hanging drop, sitting drop, sandwich drop, capillary diffusion, gel equilibration, etc. (McPherson, A., 1989, "Preparation and Analysis of Protein Crystals" R. E. Krieger Publishing Co., Malabar, Fla., USA). Diffraction data are collected from these crystals via the rotation method (Blundell, T. L., Johnson, L. N., 1976, "Protein Crystallography" Academic Press, Harcourt Brace Jovanovich, Publishers; London; Stout & Jensen, 1989, "X-ray Structure Determination, A Practical Guide" John Wiley & Sons, Publishers, New York) both on a rotating anode X-ray generator and at synchrotron sources. Crystal structures are determined by techniques standard in the field, such as molecular replacement (MR), heavy atom phasing via single isomorphous replacement (SIR), heavy atom phasing via single isomorphous replacement with anamolous scattering (SIRAS), heavy atom phasing via multiple isomorphous replacement (MIR), heavy atom phasing via multiple isomorphous replacement with anamolous scattering (MIRAS), and/or heavy atom phasing via isomorphous replacement of methionines with selenomethionine and employing "Multi-wavelength Anamolous Diffraction" (MAD) (Blundell & Johnson; supra; Stout & Jensen, supra; Bella, J.; Rossmann, M. G., 1998, Acta Crystallogr D Biol Crystallogr, 54(Pt 2), 159–74; Fanchon, E.; Hendrickson, W. A., Acta Crystallogr A Oct. 1, 1990;46 (Pt 10):809–20; Hendrickson W A; et al., Proteins, 1988 4(2), 77–88; Pahler, A.; et al., 1990, Acta Crystallographica. Section A, Crystal physics, Diffraction, Theoretical and General Crystallography, 46 (Pt 7), 537–40; Terwilliger, T. C., Berendzen, J., 1999, Acta Crystallographica, Section D, Biological Crystallography, 55(Pt 4), 849–61; and Walsh, M. A., et al., 1999 Acta Crystallogr D Biol Crystallogr, 55(Pt 10), 1726–32).

Functional Validation

In general, functional assays are used to confirm the participation of the Ect2 gene and its orthologs in p21-related pathways. Various preferred assays for functional validation of Ect2 in the p21 pathway include expression analysis, and cell transformation, proliferation, cell cycle, apoptosis, and hypoxia induction assays, among others.

A preferred functional validation assay for Ect2 is expression analysis. Several methods are available to assess whether altered Ect2 expression is correlated with tumorogenicity, or another p21-related phenotype. These include Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; BloMP21 DH and Guiseppi-Elie, A Curr Opin Biotechnol 2001, 12:41–47). In one example, Northern blot analysis of mRNA from tumor and normal cell lines, and from tumor and matching normal tissue samples from the same patients, using full or partial Ect2 cDNA sequences as probes, can determine whether particular tumors overexpress Ect2. Alternatively, the TaqMan® is used for quantitative RT-PCR analysis of Ect2 expression in cell lines, normal tissues and tumor samples (PE Applied Biosystems).

Apoptosis, cell proliferation, cell cycle, cell transformation, and hypoxia induction assays typically involve comparing these cellular events in wild type cells and cells with altered expression of an Ect2 protein. These assays may use tumor or other cells or cell lines with increased or decreased expression of an Ect2 protein, such as those identified by expression analysis, as described above. Alternatively, the assays may use cells engineered to specifically overexpress an Ect2 protein, using above-described expression methods. The assay may also use cells specifically engineered to disrupt expression of an Ect2 protein, such as by RNA inhibition (Elbashir S M et al. Nature 2001, 411: 494–498) or using antisense oligomers, as further described below.

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730–41).

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79). Cell Proliferation may also be examined using [$^3$H]-thymidine incorporation (Chen, J., 1996, Oncogene 13:1395–403; Jeoung, J., 1995, J. Biol. Chem. 270:18367–73). This assay allows for quantitative characterization of Sphase DNA syntheses. In this assay, cells synthesizing DNA will incorporate [$^3$H]thymidine into newly synthesized DNA. Incorporation can then be measured by standard techniques such as by counting of radioisotope in a scintillation counter (e.g., Beckman LS 3800 Liquid Scintillation Counter). Cell proliferation may also be assayed by colony formation in soft agar (Sambrook et al., Molecular Cloning, Cold Spring Harbor (1989)). Cells transformed with Ect2 are seeded in soft agar plates, and colonies are measured and counted after two weeks incubation.

Angiogenesis may be assayed using various human endothelial cell systems, such as umbilical vein, coronary artery, or dermal cells. The assays might include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; or tubule formation assays based on the formation of tubular structures by endothelial cells on Matrigel™ (Becton Dickinson).

Involvement of a gene in the cell cycle may be assayed by flow cytometry. Cells transfected with an Ect2 may be stained with propidium iodide and evaluated in a flow cytometer (available from Becton Dickinson).

Induction by hypoxic conditions may be assayed by growing cells transfected with MP21 in hypoxic conditions (such as with 0.1% $O_2$, 5% $CO_2$, and balance $N_2$, generated in a Napco 7001 incubator (Precision Scientific)) and normoxic conditions, followed by assessment of gene activity or expression by Taqman®.

Production of Genetically Modified Animals

The methods of this invention may use non-human animals that have been genetically modified to alter expression of Ect2 and/or other genes known to be involved in regulation of the G1 phase of the cell cycle, such as p21. Preferred genetically modified animals are mammals. Preferred non-mammalian species include Zebrafish, *C. elegans*, and Drosophila. Preferably, the altered Ect2 or other gene expression results in a detectable phenotype, such as increased or reduced cell proliferation relative to control animals having normal expression of the altered gene. The genetically modified animals can be used to further elucidate the p21 pathway, in animal models of pathologies associated with cell proliferation disorders, and for in vivo testing of candidate therapeutic agents, as described below.

Preferred genetically modified animals are transgenic, at least a portion of their cells harboring non-native nucleic acid that is present either as a stable genomic insertion or as an extra-chromosomal element, which is typically mosaic. Preferred transgenic animals have germ-line insertions that are stably transmitted to all cells of progeny animals.

Non-native nucleic acid is introduced into host animals by any expedient method. Methods of making transgenic non-human animals are well-known in the art (for mice see Brinster et al., Proc. Nat. Acad. Sci. USA 1985, 82:4438–42; U.S. Pat. Nos. 4,736,866, 4,870,009, 4,873,191, 6,127,598; Hogan, B., Manipulating the Mouse Embryo, Cold Spring Harbor Laboratory Press, Cold Spring Harbor, N.Y., (1986); for homologous recombination see Capecchi, Science 1989, 244:1288–1292; Joyner et al., Nature 1989, 338:153–156; for particle bombardment see U.S. Pat. No. 4,945,050; for Drosophila see Rubin and Spradling, Science (1982) 218:348–53, U.S. Pat. No. 4,670,388; for transgenic insects see Berghammer A. J. et al., Nature 1999, 402:370–371; for Zebrafish see Lin S. Methods Mol Biol. (2000) ;136:375–3830; for fish, amphibians and birds see Houdebine and Chourrout, Experientia (1991) 47:897–905; for rats see Hammer et al., Cell (1990)63:1099–1112; for embryonic stem (ES) cells see Teratocarcinomas and Embryonic Stem Cells, A Practical Approach, E. J. Robertson, ed., IRL Press (1987); for livestock see Pursel et al., Science (1989) 244:1281–1288; for nonhuman animal clones see Wilmut, I. et al. (1997) Nature 385:810–813, PCT Publication Nos. WO 97/07668 and WO 97/07669; for recombinase systems for regulated transgene expression see, Lakso et al., PNAS (1992) 89:6232–6236; U.S. Pat. No. 4,959,317 [for cre.loxP] and O'Gorman et al., Science (1991) 251:1351–1355; U.S. Pat. No. 5,654,182 [for FLP/FRT).

Homozygous or heterozygous alterations in the genomes of transgenic animals may result in mis-expression of native genes, including ectopic expression, over-expression (e.g. by multiple gene copies), under-expression, and non-expression (e.g. by gene knock-out or blocking expression that would otherwise normally occur). In one application, a "knock-out" animal is generated, typically using homologous recombination, in which an alteration in an endogenous gene causes a decrease in that gene's function, preferably such that gene expression is undetectable or insignificant.

Ect2-Modulating Agents

The invention provides methods to identify agents that interact with and/or modulate the function of Ect2 and/or the p21 pathway. Such agents are useful in a variety of diagnostic and therapeutic applications associated with diseases or disorders involving a defective p21 pathway, as well as in further analysis of the Ect2 protein and its contribution to the p21 pathway. Accordingly, the invention also provides methods for modulating the p21 pathway comprising the step of specifically modulating Ect2 activity by administering Ect2-interacting or -modulating agent.

In a preferred embodiment, Ect2-modulating agents inhibit or enhance Ect2 activity or otherwise affect normal Ect2 function, including transcription, protein expression, protein localization, and cellular or extra-cellular activity. In a further preferred embodiment, the candidate p21 pathway-modulating agent specifically modulates the function of the Ect2. The phrases "specific modulating agent", "specifically modulates", etc., are used herein to refer to modulating agents that directly bind to the Ect2 polypeptide or nucleic acid, and preferably inhibit, enhance, or otherwise alter the function of the Ect2. The term also encompasses modulating agents that alter the interaction the Ect2 with a binding partner or substrate (e.g. by binding to a binding partner of an Ect2, or to a protein/binding partner complex, and inhibiting function).

Preferred Ect2-modulating agents include small molecule chemical agents, Ect2-interacting proteins, including antibodies and other biotherapeutics, and nucleic acid modulators, including antisense oligomers and RNA. The modulating agents may be formulated in pharmaceutical compositions, for example, as compositions that may comprise other active ingredients, as in combination therapy, and/or suitable carriers or excipients. Methods of formulating biotherapeutic agenst are described in detail in U.S. Pat. No. 6,146,628. Techniques for formulation and administration of compounds may be found in "Remington's Pharmaceutical Sciences" Mack Publishing Co., Easton, Pa., 19$^{th}$ edition.

Small Molecule Modulators

Small molecule modulators are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Small molecule modulators may be rationally designed based on known structural properties, for example, discerned using method described above. Structures of Ect2 in complex with the partner G-protein (RhoA/Rac/CDC42) show the details of protein-protein interactions required for the GEF activity and can be used to aid in the rational design of small-molecule compounds that modulate the mechanics of these interactions, thereby disrupting the GEF functionality. Structures of Ect2 polypeptides in complex with small-molecule ligands which serve to modulate the GEF activity delineate the portions of the Ect2 molecule which are either directly involved in the catalytic active site or which exert an allosteric effect on the active site, thereby modulating the GEF activity. These modulators of Ect2/GEF activity bind within a radius of 25 Å, 20 Å, 15 Å, 10 Å, 5 Å, or 1.8 Å of certain residues, such as serine 571 ( . . . RLPSVA . . . ), thereby defining a productive binding mode that modulates GEF activity. Small molecule modulators may also be identified by screening compound libraries.

Alternative small molecule modulators include natural products, particularly secondary metabolites from organisms such as plants or fungi, which can also be identified by screening compound libraries for Ect2-modulating activity. Methods for generating and obtaining compounds are well known in the art (Schreiber S L, Science (2000) 151: 1964–1969; Radmann J and Gunther J, Science (2000) 151:1947–1948).

Small molecule modulators identified from screening assays, as described below, can be used as lead compounds from which candidate clinical compounds may be designed, optimized, and synthesized. Such clinical compounds may have utility in treating pathologies associated with the defective p21 signaling. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

An Ect2-interacting protein may be endogenous, i.e. one that normally interacts genetically or biochemically with an Ect2, such as a member of the p21 pathway that modulates Ect2 expression, localization, and/or activity. Ect2-modulators include dominant negative forms of Ect2-interacting proteins and of Ect2 proteins themselves. Yeast two-hybrid and variant screens offer preferred methods for identifying endogenous Ect2-interacting (Finley, R. L. et al. (1996) in DNA Cloning-Expression Systems: A Practical Approach, eds. Glover D. & Hames B. D (Oxford University Press, Oxford, England), pp. 169–203; Fashema S F et al., Gene (2000) 250:1–14; Drees B L Curr Opin Chem Biol (1999) 3:64–70; Vidal M and Legrain P Nucleic Acids Res (1999) 27:919–29; and U.S. Pat. No. 5,928,868). Mass spectrometry offers alternative preferred methods for the elucidation of protein complexes (reviewed in, e.g., Pandley A and Mann M, Nature (2000) 405:837–846; Yates J R 3$^{rd}$, Trends Genet (2000) 16:5–8).

An Ect2-interacting protein may be exogenous protein, such as an Ect2-specific antibody or a T-cell antigen receptor (see, e.g., Harlow and Lane (1988) Antibodies, A Laboratory Manual, Cold Spring Harbor Laboratory). Ect2 antibodies are further discussed below.

In one preferred embodiment, an Ect2-interacting protein specifically binds an Ect2 protein. In an alternative preferred embodiment an Ect2-modulating agent binds an Ect2 substrate, binding partner, or cofactor. In certain applications when Ect2-interacting proteins are used in screens to identify small molecule modulators, the binding specificity of the interacting protein to the Ect2 protein may be assayed by various known methods, including binding equilibrium constants (usually at least about $10^7$ $M^{-1}$, preferably at least about $10^8$ $M^{-1}$, more preferably at least about $10^9$ $M^{-1}$), and immunogenic properties. For enzymes and receptors, binding may be assayed by, respectively, substrate and ligand processing.

Specific antibodies

In a preferred embodiment, the Ect2-interacting protein is an antibody. Antibodies that specifically bind Ect2 polypeptides can be generated using known methods. Preferably the antibody is specific to a mammalian Ect2 polypeptide, and more preferably, a human Ect2. Antibodies may be polyclonal, monoclonal (mAbs), humanized or chimeric antibodies, single chain antibodies, Fab fragments, F(ab') .sub.2 fragments, fragments produced by a FAb expression library, anti-idiotypic (anti-Id) antibodies, and epitope-binding fragments of any of the above. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, Antibodies: A Laboratory Manual, CSH Laboratory (1988); Goding (1986) Monoclonal Antibodies: Principles and Practice (2d ed) Academic Press, New York; and U.S. Pat. Nos. 4,381,292; 4,451,570; and 4,618,577). Antibodies may be generated against extracts of cells that express Ect2 or from substantially purified Ect2 or fragments thereof. If Ect2 fragments are used, they preferably comprise at least 10, and more preferably, at least 20 contiguous amino acids of an Ect2 protein. In a particular embodiment Ect2-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of Ect2-specific antibodies is assayed by an appropriate assay such as a solid phase enzyme-linked immunosorbant assay (ELISA) using immobilized corresponding Ect2 polypeptides. Other assays, such as radioimmunoassays or fluorescent assays might also be used.

Chimeric antibodies specific to Ect2 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementary-determining regions (CDRs) (Carlos, T. M., J. M. Harlan., Blood (1994) 84:2068–2101) of mouse antibodies into a background of human framework regions and constant regions by recombinant DNA technology (Riechmann L M, et al., Nature (1988) 323:323–327). Humanized antibodies contain ~10% murine sequences and ~90% human sequences, and thus further reduce or eliminate immunogenicity, while retaining the antibody specificities (Co MS, and Queen C., Nature (1991) 351:501–501; Morrison S L., Ann. Rev. Immun. (1992) 10:239–265). Humanized antibodies and methods of their production are well-known in the art (U.S. Pat. Nos. 5,530,101; 5,585,089; 5,693,762, and 6,180,370).

Ect2-specific single chain antibodies, which are recombinant, single chain polypeptides formed by linking the heavy and light chain fragments of the Fv regions via an amino acid bridge, can be produced (U.S. Pat. No. 4,946,778; Bird, Science (1988) 242:423–426; Huston et al., Proc. Natl. Acad. Sci. USA (1988) 85:5879–5883; and Ward et al., Nature (1989) 334:544–546).

Other suitable techniques for antibody production involve in vitro exposure of lymphocytes to the antigenic polypeptides or alternatively to selection of libraries of antibodies in phage or similar vectors (Huse et al., Science (1989) 246:1275–1281).

The polypeptides and antibodies of the present invention may be used with or without modification. Frequently, the polypeptides and antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic proteins may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg–to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies'concentrations in such vehicles are typically in the range of about 1 mg/ml–to about 10 mg/ml. Immunotherapeutic methods are further described in the literature (U.S. Pat. No. 5,859,206; WO0073469).

Nucleic Acid Modulators

Other preferred Ect2-modulating agents comprise nucleic acid molecules, such as antisense oligomers or double stranded RNA (dsRNA), which generally inhibit Ect2 activity.

Preferred antisense oligomers interfere with the function of Ect2 nucleic acids, such as DNA replication, transcription, Ect2 RNA translocation, translation of protein from the Ect2 RNA, RNA splicing, and any catalytic activity in which the Ect2 RNA participates. In one embodiment, the antisense oligomer is an oligonucleotide that is sufficiently complementary to an Ect2 mRNA to bind to and prevent translation from the Ect2 mRNA, preferably by binding to the 5' untranslated region. Ect2-specific antisense oligonucleotides preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA, a chimeric mixture of DNA and RNA, derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphorothioate morpholino oligomer (PMO). PMOs are assembled from four different morpholino subunits, each of which containing one of four genetic bases (A, C, G, or T) linked to a six-membered morpholine ring. Polymers of these subunits are joined by non-ionic phosphodiamidate inter-subunit linkages. Methods of producing and using PMOs and other antisense oligonucleotides are well known in the art (e.g. see WO99/18193; Summerton J, and Weller D, Antisense Nucleic Acid Drug Dev 1997, 7:187–95; Probst J C, Methods (2000) 22:271–281; U.S. Pat. Nos. 5,325,033 and 5,378,841).

Antisense oligomers are commonly used as research reagents, diagnostics, and therapeutics. For example, antisense oligonucleotides, which are able to specifically inhibit gene expression, are often used to elucidate the function of particular genes (see, e.g., U.S. Pat. No. 6,165,790). Antisense oligomers are also used, for example, to distinguish between functions of various members of a biological pathway. Antisense oligomers have been employed as therapeutic moieties in the treatment of disease states in animals and humans and have been demonstrated in numerous clinical trials to be safe and effective (Milligan J F, et al, Current Concepts in Antisense Drug Design, J Med Chem. (1993) 36:1923–1937; Tonkinson J L et al., Antisense Oligodeoxynucleotides as Clinical Therapeutic Agents, Cancer Invest. (1996) 14:54–65). Accordingly, in one aspect of the invention, an Ect2-specific antisense oligomer is used in an assay to further elucidate the function of Ect2 in the p21 pathway. In another aspect of the invention, an Ect2-specific antisense oligomer is used as a therapeutic agent for treatment of metabolic pathologies.

Alternative preferred Ect2-modulating agents are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and mammals are known in the art (Fire A, et al., 1998 Nature 391:806–811; Fire, A. Trends Genet. 15, 358–363 (1999); Sharp, P. A. RNA interference 2001. Genes Dev. 15, 485–490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619, and Elbashir S M, et al., 2001 Nature 411:494–498).

Assay Systems

The invention provides assay systems for identifying specific modulators of Ect2 activity. In general, primary assays are used to identify or confirm a modulator's specific biochemical or molecular effect with respect to the Ect2 nucleic acid or protein. In general, secondary assays further assess the activity of an Ect2-modulating agent identified by a primary assay and may confirm that the modulating agent affects Ect2 in a manner relevant to the p21 pathway and cell cycle regulation.

Primary Assays

The type of modulator tested generally determines the type of primary assay.

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384–91 and accompanying references). As used herein the term "cell-based" refers to assays using live cells, dead cells, or a particular cellular fraction, such as a membrane, endoplasmic reticulum, or mitochondrial fraction. Cell-based screening assays usually require systems for recombinant expression of Ect2 and any auxiliary proteins demanded by the particular assay. The term "cell free" encompasses assays using substantially purified protein (either endogenous or recombinantly produced), partially purified cellular extracts, or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent (Klebe C, et al., Biochemistry (1995) 34:12543–12552), radioactive (Hart M, et al., Nature (1991) 354:311–314), calorimetric, spectrophotometric, and amperometric methods, to provide a read-out for the particular molecular event detected, often in high throughput screening (HTS) formats (for example, see Hertzberg R P, and Pope A J, Current Opinion in Chemical Biology (2000) 4:445–451).

Assays for binding agents include screens for compounds that modulate Ect2 interaction with a natural Ect2 binding target. The Ect2 polypeptide used in such assays may be fused to another polypeptide such as a peptide tag for detection or anchoring, etc. In a particular embodiment, the binding target is RhoA, RhoC, Rac, or Cdc42, or portion thereof that provides binding affinity and avidity to the subject Ect2 polypeptide conveniently measurable in the assay and preferably comparable to the intact RhoA, RhoC, Rac, or Cdc42. The Ect2 and binding target are incubated in the presence and absence (i.e. control) of a candidate Ect2 modulating agent under conditions whereby, but for the presence of the candidate modulating agent, the Ect2 polypeptide specifically binds the cellular binding target, portion or analog with a reference binding affinity. After incubation, the agent-biased binding between the Ect2 polypeptide and one or more binding targets is detected by any of a variety of methods depending on the nature of the product and other assay components, such as through optical or electron density, radiative emissions, nonradiative energy transfers, etc. or indirect detection with antibody conjugates, etc. A difference in the binding affinity of Ect2 to the target in the absence of the agent, as compared with the binding affinity in the presence of the agent indicates that the agent modulates the binding of the Ect2 to the Ect2 binding target. A difference, as used herein, is statistically significant and preferably represents at least a 50%, preferably at least 60%, more preferably 75%, and most preferably a 90% difference.

We developed a solid-phase radiometric high throughput assay format to measure activity of Ect2, and other GEFs. The GTPase/GEF activity is evaluated by measuring the binding of the activating ligand -GTP in solid phase. In this assay, the GTPase (such as Rho or Rac) is adsorbed to the bottom of commercially available plates, such as Flashplate (Perkin Elmer Life Sciences), which have scintillant coated on the bottom and sides of the wells. The plates are then washed to remove excess protein. A test compound (candidate modulating agent) is added, followed by GEF (such as ect2, or a functional Ect2 fragment such as a fragment comprising the Dbl homology domain), followed by 35S labeled GTP. When the radioisotope is associated with the solid phase it is measured in a scintillation counter just as if liquid scintillant had been added. Thus, following incubation, the plates are simply counted without further processing, since only 35S-GTP that is exchanged onto the GTPase will be detected. Unbound radioactive GTP remains in solution and is undetectable. Magnesium chloride is used as a negative control. In the absence of GEF, 2 mM $MgCl_2$ prevents GTP from binding, and thus, reduces the number of cpm/well. Inclusion of GEF in the assay will rescue the $MgCl_2$ inhibited exchange.

Other preferred assay formats use fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730–4; Fernandes P B, Curr Opin Chem Biol (1998) 2:597–603; Hertzberg R P and Pope A J, Curr Opin Chem Biol (2000) 4:445–451). We developed an FMAT (Fluorescent Microvolume Assay Technology) assay format to measure the protein-protein interaction of a GEF and GTPase, whereby GST-fused GTPase (such as RhoA, RhoC, or Rac) is attached to polystyrene beads and the GEF (such as Ect2) is labeled with Cy5 (a long wavelength fluorophore, available from Amersham). When the GTPase and the GEF are associated, there is an increase in fluorescence associated with GTPase beads, which settle to the bottom of the well and are detected using an FMAT 8100 HTS system (Applied Biosystems). Potential inhibitors interfere with the GEF-GTPase association with subsequent decrease in fluorescence.

For antibody modulators, appropriate primary assays test the antibody's specificity for and affinity to the Ect2 protein. Methods for testing antibody specificity and affinity are well known in the art. Alternatively or additionally, primary assays for antibody modulators may comprise the screening assays described above, used to detect the Ect2 modulator's specific activity.

For nucleic acid modulators, primary assays may test the ability of the nucleic acid modulator to inhibit Ect2 mRNA or protein expression. In general, expression analysis comprises comparing Ect2 expression in like populations of cells (e.g., two pools of cells that endogenously or recombinantly express Ect2) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that Ect2 mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm D H and Guiseppi-Elie, A Curr Opin Biotechnol 2001, 12:41–47). Proteins are most commonly detected with specific antibodies or antisera directed against either the Ect2 protein or specific peptides. Protein expression can be monitored using by a variety of means including Western blotting, the enzyme-linked immunosorbent assay (ELISA), or in situ detection (Harlow E and Lane D (eds.) Using Antibodies: A Laboratory Manual, 1999, Cold Spring Harbor Laboratory Press, New York).

Secondary assays

Secondary validation can use essentially the same assays used to functionally validate the participation of an ect2 gene in a p21 related pathway. Whereas the afore-described functional validation assays generally compare cells expressing altered levels of an Ect2 protein, secondary validation assays generally compare like populations of cells (e.g., two pools of wild type cells) in the presence and absence of the candidate modulator.

In another embodiment, secondary validation may use the same assays used for high throughput screening. These methods can confirm the activity of a modulator not identified through high throughput screening, such as an antibody or an antisense oligonucleotide modulator, or can confirm the activity of a small molecule modulator identified using a different high throughput screening assay. These assays may also be used to confirm the specificity of a candidate modulator.

Additionally, the modulator is assayed for its effectiveness on the Ect2 in a p21 related manner. Such assays include cell cycle, apoptosis, proliferation, and hypoxic induction assays, among others, as described above. To assess the role of modulators, these assays are performed in presence or absence of the modulator in p21 normal and p21 mutated backgrounds. These assays may use cell lines deficient in p21 such as HCT116 colon cancer cells, among others, available from ATCC (American Type Culture Collection, Manassas, Va.).

Therapeutic and diagnostic applications

When used for anti-tumor therapy in a patient, Ect2 modulating agents are administered to the patient in therapeutically effective amounts that eliminate or reduce the patient's tumor burden. They will normally be administered parenterally, when possible at the target cell site, or intravenously. The dose and dosage regimen will depend upon the nature of the cancer (primary or metastatic), its population, the target site, the characteristics of the particular immunotoxin (when used), e.g., its therapeutic index, whether the agent is administered in combination with other therapeutic agents, and the patient's history. The amount of agent administered will typically be in the range of approximately 0.1–10 mg/kg of patient weight.

For parenteral administration, the agents will be formulated in a unit dosage injectable or inhalable (solution, suspension, emulsion) form in association with a pharmaceutically acceptable vehicle, typically in a concentration of about 1–10 mg/ml.

Antibodies that specifically bind Ect2 may be used for the diagnosis of conditions or diseases characterized by expression of Ect2, or in assays to monitor patients being treated with Ect2 modulating agents. Diagnostic assays for Ect2 include methods which utilize the antibody and a label to detect Ect2 in human body fluids or extracts of cells or tissues. The antibodies may be used with or without modification, and may be labeled by joining them, either covalently or non-covalently, with a reporter molecule.

Diagnosis of conditions characterized by expression of Ect2 may also be accomplished by any of a variety of methods such as Northern or TaqMan® analysis (discussed supra) to measure expression of Ect2 in patient samples.

The following experimental section and examples are offered by way of illustration and not by way of limitation.

EXAMPLES

I. High throughput fluorescent or radioactive homogeneous assay

Various combinations of fluorescently (with N-Methylanthraniloyl, Bodipy or other commonly used fluorophores) or radioactively (3H, 35S, or 33P) labeled GTP, GDP, dGTP, or dGTP and ect2 are added to each well of a 96-well plate, along with a test compound of choice. Fluorescent measurements (of over 500 nm to reduce background fluorescence) or radioactivity measurements indicative of the exchange reaction are then taken.

The above assay may be performed where all components are in solution, or alternatively, where at least one component is attached to beads that are 10 nm or larger in diameter (such as SPA beads from Amersham, Alpha screen beads from Packard, or FMAT beads from PE Biosystems).

II. High throughput Elisa format assay

Various combinations of Glutathione-S-transferase/ RhoA, Rhoc, RAC, or CDC42 polypeptide fusion protein and biotinylated Ect2 are added to each well of a microtiter plate (Reacti-Bind Streptavidin-Coated, White Polystyrene Plates (#15118B), which have been blocked by Super-Blocking Reagent from Pierce) in assay buffer (0.01M HEPES, 0.15M NaCl, 0.002M $MgCl_2$). Test compounds are then added to each well, and incubated at room temperature for 1 hour. Anti-GST, rabbit and anti-rabbit antibodies are then added to each well and incubated on ice for 1 hour. Plates are then washed with water, diluted Supersignal substrate is added to each well, and chemiluminescence is then measured.

III. Solid Phase Rac1-dbl screen

3×30 plates/day

Day 1

Reconstitute 4×10 mg GST-Rac1 in 4×10 ml Assay Buffer

Prepare 3 L Assay Buffer (to 1 L 1.4 mM Tris pH7.5, 5 mM MgCl$_2$, 0.3% sucrose, 0.1%
dextran add 1 ml 1M DTT/L)
Dilute GST-Rac1 into 100 ml Assay Buffer
Mix
Dilute into 1 L Assay Buffer
Mix
Dilute into 2 L Assay Buffer.
Giving a final volume of 2 L of 10 ug/ml GST-Rac1 in Assay Buffer.
Coat 90 Flashplates (Perkin Elmer Life Sciences) with 0.5 ug/well GST-Rac1
(50 ul of 10 ug/ml GST-cdc42 in Assay Buffer)
Place at 4° C. overnight
Prepare 2 L TBS (50 mM Tris-HCl, pH 7.4, 150 mM NaCl).
Day 2.
Thaw 1 vial (1 mCi) [$^{35}$S]GTPγS.
Wash 30 GST-cdc42 coated plates 3×70 ul TBS
Dilute compound in plates by addition of 10 ul Assay Buffer
Transfer 5 ul compound dilution to assay plates
Prepare 0.1 L of Assay buffer containing 1 mCi [$^{35}$S] GTPγS, 500 nM Dbl
Add 5 ul/well dbl/GTPγS (columns 1&2 receive buffer alone)
Seal
Incubate @ room temp×1 hour
Count in the Trilux Scintillation counter Prepare the remaining 2×30 plates as described above and store at room temp.

IV. FMAT GEF assay 0.5 ml Protein G polystyrene beads (7 u, 0.5% w/v Spherotech [Libertyville, Ill.]) are washed three times with PBS and resuspended in 0.5 ml PBS. For monitoring of biomolecular binding events, Anti-GST (0.25 ug BIAcore [Uppsala, Sweden]) is added and incubated at room temperature for 30 minutes. The beads are then washed three times with PBS and resuspended in 0.5 ml PBS. The sample is split into 2×0.25 ml aliquots and 2.5 ug of either GST or GST-RhoA is added and incubated at room temperature for 30 minutes. The beads are then washed three times with PBS and resuspended in 0.25 ml PBS.

(His)6 tagged Ect2-dbl domain is labeled with Cy 5 using a Cy5 monoclonal antibody labeling kit according to the manufacturers instruction (Amersham).

To 400 ul of PBS add 4 ul of either "RhoA-beads" or "GST-beads" giving a final concentration of 20 nM RhoA or GST. Add 200 nM Cy5-Ect2_dbl. Mix and aliquot 8×50 ul into a 96 well FMAT plate. Incubate at room temperature for 1 hour and read in the Cy5 detecting channel of an FMAT 8100 HTS system.

All references cited herein, including sequence information in referenced Genbank identifier numbers and website references, are incorporated herein in their entireties.

What is claimed is:

1. A purified ECT2 polypeptide having GEF activity and comprising an amino acid sequence consisting of SEQ ID NO:4.

* * * * *